（12）United States Patent
Sakaino et al.

(10) Patent No.: US 7,820,402 B2
(45) Date of Patent: Oct. 26, 2010

(54) IMMUNOASSAY ELEMENT

(75) Inventors: Yoshiki Sakaino, Saitama (JP); Hitomi Ito, Saitama (JP); Toshihiro Mori, Saitama (JP); Osamu Seshimoto, Saitama (JP); Toshihisa Ito, Saitama (JP); Yoshikazu Amano, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 937 days.

(21) Appl. No.: 11/230,127

(22) Filed: Sep. 19, 2005

(65) Prior Publication Data

US 2006/0024770 A1 Feb. 2, 2006

(51) Int. Cl.
*G01N 33/53* (2006.01)
*G01N 33/543* (2006.01)

(52) U.S. Cl. ............ 435/7.9; 435/7.91; 435/7.92; 435/14; 435/18; 435/22; 435/25; 435/28; 435/966; 435/969; 435/970; 436/518; 436/528; 436/531; 436/537; 436/807; 436/810; 422/56; 422/57

(58) Field of Classification Search ............ 435/7.9, 435/7.91, 7.92, 14, 18, 22, 28, 25, 966, 969, 435/970; 436/518, 528, 531, 537, 807, 810; 422/56, 57
See application file for complete search history.

(56) References Cited

U.S. PATENT DOCUMENTS 5,569,589 A * 10/1996 Hiraoka et al. ............ 435/7.9

* cited by examiner

*Primary Examiner*—Jacob Cheu
*Assistant Examiner*—Pensee T Do
(74) *Attorney, Agent, or Firm*—Buckley, Maschoff & Talwalkar LLC

(57) ABSTRACT

The immunoassay element for quantitatively analyzing an antigen by determining the change in enzymatic activity of an enzyme-labelled antigen or antibody caused by an immunological reaction. The immunoassay element comprises a substrate layer containing a non-diffusible substrate which forms a diffusible material in the presence of the labelling enzyme, and a reagent layer containing a fragmenting enzyme for further fragmenting the diffusible material into a lower molecular weight product. As the non-diffusible substrate, a substrate capable of reacting solely with the labelling enzyme and incapable of reacting the fragmenting enzyme is utilized. When an endo-active glucosidase is used as the labelling enzyme, and an exo-active glucosidase is used the fragmenting enzyme in the reagent layer, the non-diffusible substrate of the substrate layer is preferred to be an endo type selectively reactive substrate, which means a substrate having a reactivity specific to endo-active glucosidase. Highly sensitive assay is realized with high accuracy and high reproducibility and good storage stability.

23 Claims, 4 Drawing Sheets

IMMUNOASSAY ELEMENT

BACKGROUND OF THE INVENTION

1. Field of the Invention

The present invention relates to a dry immunoassay element in which a homogeneous enzyme immunoassay is utilized. More particularly, the present invention relates to an immunoassay element comprising a substrate layer containing a non-diffusible substrate which forms a diffusible material in the presence of a labelling enzyme and a reagent layer containing a fragmenting enzyme for further fragmenting the diffusible material into lower molecular weight product, wherein the non-diffusible substrate is a substrate which selectively reacts with the labelling enzyme and avoids reacting with the fragmenting enzyme.

2. Description of the Related Art

Analyses of the constituents originated from the living body or chemicals contained in the body fluids, such as blood and urine, are useful for diagnosing the condition of diseases or judging the course of curing, and thus they occupy important parts in the field of clinical test. The so-called enzyme immunoassay has been known in the art as one method for analyzing such constituents (ligands) generally present in a small amount in the body fluids. The enzyme immunoassay may be classified into heterogeneous systems for which B/F (Bound/Free) separation must be effected, and homogeneous system for which B/F separation is not necessary. The reactions in the homogeneous system are based on the phenomenon that the enzymatic activity of the labeling enzyme is affected by some interference caused by binding of an antibody to the antigen (ligand), and the inhibition due to antigen-antibody binding is generally utilized. It is considered that the enzymatic activity is suppressed by a steric hindrance caused by binding the enzyme to the substrate or a change in three-dimensional structure of the enzyme, when the antibody which is generally a large molecule is bound to the antigen in the enzyme-labelled antigen.

When the antigen is a high polymer, suppression of enzymatic activity by the antigen-antibody binding reaction may be detected by labelling the antibody with an enzyme.

Meanwhile, in the routine clinical tests in which a number of test samples are to be handled, it is demanded that the individual samples should be analyzed by simple operations, more desirously by automated operation sequence.

To comply with the demand, dry analysis elements have been proposed (see, for example, Unexamined Japanese Patent Publication Nos. 53888/1974 (Corresponding to U.S. Pat. No. 3,992,158), 90859/1980 (corresponding U.S. Pat. No. 4,258,001), 164356/1980 (U.S. Pat. No. 4,292,272), 222769/1985 (EP 0162302A), 77356/1984 (corresponding to EP 0097952A), 102388/1984 and 501866/1986 (U.S. Pat. No. 4,459,358.)

A dry analysis element has been known, in which an enzyme-labelled antibody is utilized and reacted in a homogeneous enzyme immunological reaction (see Unexamined Japanese Patent Publication No. 321360/1989 which corresponds to EP 0347839A). This known dry analysis element comprises the following three reagent ingredients in the same or different layers in the composite multi-layered structure:

(A) An antigen having a high molecular weight (a coupling product of a ligand or a derivative thereof with a high molecular weight compound; hereinafter referred to as "polymerized antigen");

(B) A water-insoluble high polymer substrate; and (C) A conjugate of an antibody against the ligand and an enzyme for the substrate.

The antigen supplied by spotting onto the analysis element binds to the antibody-enzyme conjugate through a competitive reaction with the reaction of the polymerized antigen. The complex of antigen-antibody-enzyme reacts with the water-insoluble high polymer substrate to form a soluble lower molecular weight product. On the other hand, the complex of polymerized antigen and enzyme-labelled antibody formed by the binding with the polymerized antigen cannot exhibit the enzymatic activity to the high polymer substrate. Accordingly, as the quantity of the antigen in the sample is increased, the product produced by the enzymatic reaction increases. This product is allowed to diffuse into a detection layer where the quantity of the product is determined by measuring the optical density of an absorption resulted by the colored chemical group, to make it possible to analyze the antigen in the sample quantitatively.

The immunoassay element disclosed in Japanese Patent No. 2576910 (corresponding to U.S. Pat. No. 5,569,589 and EP 0451848A) is an improvement of the aforementioned immunoassay element. This immunoassay element has a reagent layer containing a fragmenting enzyme for further fragmenting the decomposition product by the reaction of labelling enzyme, so that the fragmented lower molecular weight product is detected for further sensitization of the element.

When the analyte or ligand is a macromolecular antigen, the immunoassay element described in the specification of Japanese Patent No. 2576913 (corresponding to U.S. patent application Ser. No. 07/763,198) may be used. This prior art element has the following two components either in a same layer or in different layers:

(A) Water-insoluble high polymer substrate; and (B) Conjugate of an antibody to the macromolecular antigen and an enzyme for the substrate.

Likewise to the immunoassay element described in the specification of Japanese Patent No. 2576910 (U.S. Pat. No. 5,569,589) a reagent layer containing a fragmenting enzyme for further fragmenting the decomposition product by the action of labelling enzyme is provided so that the fragmented product having a lower molecular weight is detected to improve the sensitivity.

In any event, the non-diffusible substrate will not migrate into the reagent layer. Further, it has been believed that the fragmenting enzyme will never migrate backward from the reagent layer to the substrate layer which overlies it. It has been heretofore customary, therefore, to deny that the substrate specificity of a non-diffusible substrate is very important and therefore to select any non-diffusible substrate which can react at all with both fragmenting enzyme and labelling enzyme.

An assay element on which a sample solution has applied, however, suffers diffusion of a soluble component, if only to a slight extent, from the lower reagent layer to the upper substrate layer. The present inventors' study of this diffusion has revealed that very small amount of the fragmenting enzyme migrates from the reagent layer to the substrate layer on the upstream side and reacts with the non-diffusible substrate to form a low molecular weight product, and that this product constitutes itself a noise hardly deserving to be ignored. Heretofore, such noise has had the possibility of degrading the accuracy of assay.

Further, the macromolecular substrate retained as a non-diffusible substrate in the substrate layer happens to contain a substrate of a low polymerization degree or a substrate of an unduly small particle diameter as an extraneous component or impurities, in a minute amount. Some of this macromolecular substrate inevitably migrates from the upper substrate layer to the lower reagent layer in consequence of the advance of supply of the sample solution. The macromolecular substrate thus migrated in a minute amount is destined to react with the fragmenting enzyme in the reagent layer and the product of this reaction is also fated to form a cause of noise.

The present inventors, thereupon, have prepared an immunoassay element by using as a non-diffusible substrate such a substrate as reacts solely with a labelling enzyme and avoids reacting with a fragmenting enzyme and then studied this immunoassay element to determine the quality thereof, to find that this immunoassay element is superior to the conventional immunoassay element not only in sensitivity but also in reproducibility and durability of aging (storage stability).

OBJECTS AND SUMMARY OF THE INVENTION

The present invention has been accomplished on the basis of this knowledge and an object thereof is to provide an immunoassay element for enabling a high sensitive analysis of an analyte with the highest possible accuracy and reproducibility and having high storage stability.

The object of this invention described above is accomplished by an immunoassay element for quantitatively analyzing an antigen by determining the change in enzymatic activity caused by any of
1) a reaction between the antigen and an enzyme-labelled antibody;
2) a reaction between the antigen, an antibody and an enzyme-labelled antigen; and
3) a reaction between the antigen, an enzyme-labelled antibody and a conjugate of the antigen with a high molecular weight compound;

wherein said element comprises a substrate layer containing a non-diffusible substrate which forms a diffusible material in the presence of said labelling enzyme, and a reagent layer containing a fragmenting enzyme for further fragmenting said diffusible material into a lower molecular weight product:
characterized in that said non-diffusible substrate is a substrate which reacts solely with said labelling enzyme and avoids reacting with said fragmenting enzyme.

In a case that the subject for assay is an antibody, the object of this invention mentioned above is accomplished by an immunoassay element for quantitatively analyzing an antibody by determining the change in enzymatic activity caused by a reaction between the antibody and an enzyme-labelled antigen or a reaction between the antibody, an antigen and an enzyme-labelled antibody, wherein said element comprises a substrate layer containing a non-diffusible substrate which forms a diffusible material in the presence of the labelling enzyme, and a reagent layer containing a fragmenting enzyme for further fragmenting said diffusible material into a lower molecular weight product:
characterized in that said non-diffusible substrate is a substrate which reacts solely with said labelling enzyme and avoids reacting with said fragmenting enzyme.

To be specific, in the immunoassay element of the present invention, a substrate capable of reacting solely with a labelling enzyme of an antigen (or an antibody) and incapable of reacting with a fragmenting enzyme contained in the reagent layer is used as a non-diffusible substrate contained in a reagent layer. As a result, the decomposition of the non-diffusible substrate by the fragmenting enzyme is nulled and the noise is consequently abated even when the fragmenting enzyme is diffused from the reagent layer into the substrate layer on the upstream side after the sample solution has been supplied by spotting. Even when the non-diffusible substrate happens to contain extraneously such an insoluble macromolecular substrate as is not retained in the substrate layer but is migrated into the reagent layer because of an unduly low polymerization degree or an unduly small particle diameter, this insoluble macromolecular substrate will not react with the fragmenting enzyme in the reagent layer. The use of this non-diffusible substrate results in improving the analyses in reproducibility and storage stability of the element.

When an endo-active glucosidase is used as the labelling enzyme of an antigen (or an antibody), and an exo-active glucosidase is used the fragmenting enzyme in as the reagent layer, the non-diffusible substrate of the substrate layer is preferred to be an endo type selectively reactive substrate, which means a substrate having a reactivity specific to endo-active glucosidase.

Alternatively, an insoluble polysaccharide having non-reducing glucose terminal glucose positioned at the branching point of glucose chain may be used as the non-diffusible substrate having a reactivity specific to endo-active glucosidase.

One of preferable examples of the endo type selectively reactive substrate is the carboxylmethylated starch which has been subjected to the limited decomposition with an exo-active glucosidase from the non-reducing terminal glucose site through the carboxymethyl-modified glucose unit site. By using the restrictively decomposed carboxylmethylated starch, it is made possible to heighten further the reactivity with the labelling enzyme and exalt the sensitivity of assay.

In a preferred embodiment, such a macromolecular polysaccharide as starch is used as the non-diffusible substrate, the labelling enzyme for an antigen or an antibody is to be an endo-active glucosidase which decomposes the macromolecular polysaccharide to a glucose oligomer, and the fragmenting enzyme is to be an exo-active glucosidase which further decomposes the oligomer into a glucose monomer.

DESCRIPTION OF THE PREFERRED EMBODIMENTS

Figure 1:
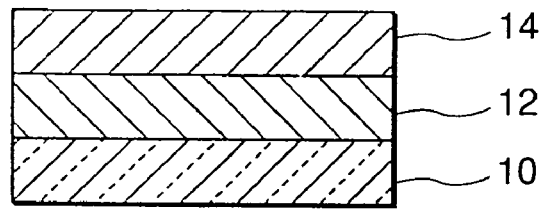
FIG. 1 is an illustration showing the principal layer structure of one embodiment of the immunoassay element of the present invention.

Layer Construction of Immunoassay Element:

FIG. 1 shows an embodiment of the immunoassay element according to this invention. In this Figure, reference numeral 10 designates a transparent support on which laminated are reagent layer 12 and a substrate layer 14.

The substrate layer 14 is composed of a water-permeable material and contains a non-diffusible substrate for a labelling enzyme which forms a conjugate with the antibody or the antigen.

The reagent layer 12 is composed of a water-permeable material and contains a reagent composition for detecting the diffusible material which has been diffused or migrated from the substrate layer. The reagent layer 12 further contains a fragmenting enzyme for further fragmenting the diffusible material into a lower molecular weight product, so that the reagent composition detects the thus formed lower molecular weight product.

The principal structure of the immunoassay element of the invention, as described in the preceding paragraph, is identical irrespective of whether the analyte is a low molecular weight antigen or a high molecular weight antigen. However, when the analyte is a low molecular weight antigen, the mixture is spotted on or otherwise supplied to the substrate layer 14, the mixture containing the reaction product of low molecular weight antigen in the sample with the enzyme-labelled antibody and the polymerized antigen (i.e., the linked product of the antigen and the high molecular weight compound). Or the analyte antigen is mixed with the antibody and the enzyme-labelled antigen to cause a competitive reaction, and the resultant reaction mixture is spotted or supplied to the substrate layer to effect the analysis. In any cases, the amount of the formed diffusible material is increased as the amount or content of the ligand (low molecular weight antigen) is large or high.

On the other hand, when the analyte is a high molecular weight or macromolecular antigen, the antigen-antibody binding reaction is effected only between the analyte and the enzyme-labelled antibody, and the reaction mixture is spotted on or otherwise supplied to the substrate layer 14. In this case, the amount of the formed diffusible material is decreased as the amount of the ligand (macromolecular antigen) is large.

When the analyte is an antibody, the assay is effected by spotting or supplying to the substrate layer 14 a mixed solution which is obtained by mixing the analyte antibody with an enzyme-labelled antigen and allowing them to react with each other. In this case, the amount of the diffusible material to be formed decreases as the amount of the analyte antibody is large or high. The assay is otherwise is effected by spotting or supplying to the substrate layer 14 a mixed solution which is obtained by mixing the analyte antibody with an antigen and an enzyme-labelled antibody and allowing them to undergo a competitive reaction. In this case, the amount of the diffusible material to be formed increases in proportion as the amount of the analyte antibody to be used increases.

Analyte (Substance to Be Analyzed)

The substance to be analyzed by the present invention (hereinafter referred simply as "analyte") is an antigen or an antibody. The antigen is a ligand having an antigenic determinant and contained in the sample.

The sample containing the analyte is not limited and many kinds of sample may be analyzed by this invention, the typical examples including blood (whole blood, blood plasma, blood serum), lymph fluid and urine. It is preferred to preclude suspended particles, such as blood cells, when such particles are present. However, a sample may be directly spotted on the analysis element of this invention without precluding such suspended particles when the analysis element has a filter layer, according to a preferred embodiment of this invention.

Any ligands, including from low molecular weight substance to high molecular weight substance, can be analyzed by the use of the analysis element of this invention, as far as each ligand acts as an antigen and an antibody therefor can be provided. Incidentally, the expression "the ligand has antigenicity" means that it is capable of reacting with a corresponding antibody and the ligand is only required to possess an epitope. Even a ligand which lacks immunogenicity in itself can serve as a ligand to be analyzed contemplated by this invention so long as it is capable of producing an antibody on being immunized as a hapten.

Examples of low molecular weight antigen include medicines such as digoxin, theophylline, phenobarbital, phenyloin, penicillin, amikacin, derivatives of these medicines (for example, complexes of medicines with living components, such as proteins), prostaglandin and hormones such as testosterone, progesterone and thyroxine.

Examples of macromolecular weight antigen include hormones secreted from various endocrine glands, plasma proteins such as immunoglobulin, albumin, ferritin, HCG (human chorionic gonadotropin) and C-reactive proteins (hereinafter referred to as CRP), viruses such as HB antigen, bacteria, and antigens present in various organs, blood and urine such as protein and α-phetoprotein and carcinoembryonic antigen (CEA).

When the ligand to be analyzed is an antigen having a high molecular weight such that the ligand, on labelled with an enzyme, manifests an interfering (inhibiting) action on the enzymatic activity of the labelling enzyme, it suffices to select other low molecular substance having an epitope common to that of the ligand and use the conjugate of such substance and the labelling enzyme as an enzyme-labelled antigen, as will be described specifically herein below. The term "enzyme-labelled antigen" as used herein represents a concept which embraces not only what is obtained by labelling the ligand (analyte antigen) with an enzyme but also what is obtained by labelling a substance having an epitope common to that of the ligand with an enzyme. Not only such compounds as ligand derivatives which are analogues in terms of chemical structure but also such compounds as behave similarly to ligand in terms of immune responsivity to an antibody can be labelled with an enzyme and used as an enzyme-labelled antigen.

Meanwhile, the high polymer antigens as referred to throughout the specification include antigens each having such a high molecular weight as exerting an interfering (suppressing) action on the enzymatic activity of the labelling enzyme, for instance, having a molecular weight of not less than 20,000 daltons, more preferably not less than about 50,000 daltons. On the other hand, the low molecular weight antigens as referred to throughout the specification include antigens each having a molecular weight low enough not to affect the enzymatic activity of the enzyme-labelled antibody, for instance, having a molecular weight of less than 20,000 daltons. However, it should be noted here that the aforementioned specific numerical value is a tentative dividing line and that the judgment on the recognition of whether one ligand is a low molecular weight antigen or a high molecular weight antigen should be made in consideration of the system whether the competition reactions between the specific analyte antigen and a certain linked product of a high polymer compound (polymerized antigen) are utilized or not.

Polymerized Antigen

The polymerized antigen, i.e., the linked product of the ligand and a large molecule or high molecular weight compound, is bound to an antibody to suppress the activity of the enzyme which is conjugated with the antibody for labelling the latter. The polymerized antigen is used when the analyte is a low molecular weight antigen, and is not used when the analyte is a high molecular weight antigen.

It is preferable that the used high molecular weight compound is water-soluble and has a molecular weight of not less than 50,000 daltons. Examples of usable high molecular weight compound are proteins such as gelatin, hemocyanin and ferritin, and polyethylene glycol. It suffices that these compounds satisfy the aforementioned conditions when bound to the ligands, and those having relatively lower molecular weights, such as bovine serum albumin, can also be used by polymerizing them, for example, by auto-polymerization.

The method for linking the ligand to the high molecular weight compound may be selected in considering the functional groups of the both reactants. Utilizable functional groups include, for example, amino, carboxyl, hydroxyl, thiol, imidazole and phenyl. For example, amino groups may be linked to each other by a number of known methods, such as isocyanate method, glutaraldehyde method, difluorobenzene method and benzoquinone methods. An amino groups may be linked to a carboxyl group by a method in which the carboxyl group is converted to succinylimide ester, or by other methods including the carbodiimide method, Woodward reagent method and the periodic acid oxidation method (Nakane method) in which the amino group is linked with a sugar chain. When a thiol group is utilized, one of the carboxyl groups is converted to succinylimide ester which is reacted with cysteine to introduce a thiol group and then both groups are linked to each other using a bifunctional linking reagent which reacts with the thiol group. The methods in which the phenyl group is utilized include the diazotization method and the alkylation method. The linking method is not limited to the aforementioned methods, and may be selected from the methods described in "Method in Immunology and Immunochemistry", vol. 1, (C. A. Williams, M. W. Chase, Academic Press (1967)) or "KOSO MEN'EKI SOKUTEI-HO" (Enzyme Immunoassay), edited by Ishikawa, Kawai and Miyai, Igaku Shoin, 1978. The ligand may be linked to the high polymer compound at any desired ratio. After the completion of the linking reaction, the reaction product is refined by the gel filtration or the ion exchange chromatography, and may be dried by the lyophilizing process as desired.

The ligand per se may be polymerized to obtain a polymerized antigen. Polymerization of the ligand may be effected similar to the aforementioned linking methods. For example, the ligand may be polymerized by using a bifunctional cross-linking agent such as carbodiimide or glutaraldehyde.

In lieu of the ligand, the high molecular weight compound may be linked to a derivative of the ligand having immunological cross-reactivity to a corresponding antibody for the ligand. Meanwhile, the derivatives of the ligand include not only those which have analogous chemical structures but also those which exhibit analogous behaviors in their immunological reactivities. For instance, when an antibody against theophylline as the ligand cross-reacts immunologically with caffeine, derivatives of caffeine may also be used as materials for forming the polymerized antigen.

When the ligand or a derivative thereof has not a proper functional group to be linked to a high molecular weight compound, an amino group, a carboxyl group or a thiol group may be introduced into the ligand or the derivative thereof. Such a group may be introduced through a spacer to facilitate linking thereof to a high molecular weight compound. For example, when the ligand is theophylline, a carboxyl group may be introduced to obtain 8-propylcarboxyl-theophylline which is linked to a high molecular weight compound.

Antibody

The antibody is used in the assay system in which the sample containing the analyte antigen is mixed with the antibody and the enzyme-labelled antigen to cause a competitive reaction. A specific antibody against the ligand which is an analyte is used for such assay system. When a derivative of the ligand is used for preparing the enzyme-labelled antigen, an antibody which reacts with the antigenic determinant common to the ligand and the derivative thereof is used. The antibody may be a polyclonal antibody obtained by the conventional process, a monoclonal antibody may be preferably used to improve the sensitivity. The antibody may be a protein fragment, such as $F(ab')_2$, Fab' or Fab.

Enzyme-Labelled Antigen

The enzyme-labelled antigen is used when a sample containing an analyte antigen is mixed with an antibody and an enzyme-labelled antigen and they are wished to undergo a competitive reaction. It is also used when the sample containing the analyte antibody is mixed with the enzyme-labelled antigen, they are allowed to undergo a binding reaction, and the amount of the antigen is determined on the basis of the change in activity of the labelling enzyme.

When the analyte is an antigen (ligand), the enzyme-labelled antigen is the linked product of the ligand (or a ligand-like substance which shares an epitope with the ligand) and an enzyme. When the ligand is such a low molecular substance as a medicine, it may be directly bound to an enzyme. When the ligand is a substance having large molecular weight such as a protein which, on being bound in its unmodified form with an enzyme, interferes with the enzymatic activity, the protein may be fragmented and a fragment thereof may be used as a substance labelled with an enzyme.

The protein thus fragmented and consequently allowed to acquire a lowered molecular weight is only required to share an epitope with the intact protein (namely, the ligand).

The ligand and the enzyme may be conjugated by the same method as adopted for the linking between the antigen (ligand) and the high molecular weight compound mentioned above.

In lieu of the ligand, the enzyme may be linked to a derivative of the ligand having immunological cross-reactivity to a corresponding antibody for the ligand. Meanwhile, the derivatives of the ligand include not only those which have analogous chemical structures but also those which exhibit analogous behaviors in their immunological reactivities. For instance, when an antibody against theophylline as the ligand cross-reacts immunologically with caffeine, derivatives of caffeine may also used as materials for forming the enzyme-labelled antigen.

When the ligand or a derivative thereof has not a proper functional group to be linked to an enzyme, an amino group, a carboxyl group or a thiol group may be introduced into the ligand or the derivative thereof. Such a group may be introduced through a spacer to facilitate linking thereof to an enzyme. For example, when the ligand is theophylline, a carboxyl group may be introduced to obtain 8-propylcarboxyl-theophylline which is linked to an antigen.

Enzyme-Labelled Antibody

The enzyme-labelled antibody is used when a given sample containing an antibody as an analyte is mixed with an antigen and an enzyme-labelled antibody and they are wished to undergo a competitive reaction. It is also used when the sample containing the antigen as an analyte is mixed with the enzyme-labelled antibody, they are allowed to undergo a binding reaction, and the amount of the antigen is determined on the basis of the change in activity of the labelling enzyme. When the analyte antigen is a low molecular weight substance, the enzyme-labelled antibody is used for causing a competitive reaction of the antigen contained in the sample with a polymerized antigen and the enzyme-labelled antibody.

In the reaction system in which the competitive reaction takes place between the analyte antibody, the antigen and the enzyme-labelled antibody, the antibody to be labelled with the enzyme is required to be capable of recognizing and reacting with an epitope of the antigen, which should be the same as the epitope recognized by the analyte antibody.

In the reaction system in which the competitive reaction is wished to be carried out between the analyte antigen, the polymerized antigen, and the enzyme-labelled antibody, the antibody to be labelled with the enzyme is required to be capable of reacting with an ideoptope which is common to the antigen and the polymerized antigen.

The antibody and the enzyme may be conjugated by the same method as adopted for the linking between the antigen (ligand) and the macromolecular substance mentioned above.

Labelling Enzyme, Non-Diffusible Substrate and Fragmenting Enzyme

The enzyme bound to the antigen or the antibody as the label decomposes the non-diffusible high polymer substrate to produce a diffusible product, which may be fragmented or decomposed to a yet lower molecular weight product (for example, glucose) by the action of the fragmenting enzyme.

The non-diffusible substrate is not dispersible into an aqueous sample liquid and neither diffused nor migrated into the reagent layer 12 by itself.

The fragmenting enzymes contained in the reagent layer 12 and converts the diffusible product produced from the non-diffusible substrate by the action of the labelling enzyme bound to the antigen (or the antibody) to form a lower molecular product which can be detected.

A suitable combination of enzyme and substrate may be selected so that an enzyme acts on the non diffusible substrate to form a diffusible substance which is further decomposed by the fragmenting enzyme to produce a lower molecular weight product which is easily detected.

Labelling Enzyme

Examples of suitable enzyme (labelling enzyme) include hydrolases which form diffusible oligomers from non-diffusible substrates composed of polymers, a specific example being glucosidase. Examples of glucosidase includes endo-active glucosidases such as α-amylase, β-amylase, and dextranase.

It is preferred that the enzyme is not affected by any hindering factor present in the sample, and that a competitive enzyme of same kind is not present in the sample. However, when an enzyme which is same as the labelling enzyme is present in the sample, an enzyme inhibitor may be used. The enzyme inhibitor may be one which inhibits the enzyme in the sample to a greater extent than the inhibiting activity towards the labelling enzyme. It is most preferable that the enzyme inhibitor entirely inactivates the enzyme in the sample and does not deactivate the labelling enzyme. However, in practical use, it suffices that the blank value is not raised at the determination step and the enzyme inhibitor may be inactivated to restore the activity of the enzyme in the sample after the completion of determination. It also suffices if the enzyme inhibitor does not inhibit the enzyme in the enzyme-labelled antigen or antibody, but can inhibit the activity of free enzyme. The enzyme inhibitor may be selected from known enzyme inhibitors so that the selected enzyme has the specific characteristics as aforementioned. Otherwise, an antibody against the enzyme which contained in a sample to cause a problem is prepared and used as an enzyme inhibitor.

Non-Diffusible Substrate

Examples of the substrate for said .alpha.-amylase, .beta.-amylase or dextranase are carboxymethylated starch (also referred to as "CM-starch" hereinafter), starch, amylose and amylopectin.

It is provided, however, that the present invention uses as the non-diffusible substrate such a substrate as reacts solely with the labelling enzyme of the antigen (or antibody) and avoids reacting with the fragmenting enzyme contained in the reagent layer. As a result, the decomposition of the non-diffusible substrate by the fragmenting enzyme is nulled and the noise is consequently abated even when the fragmenting enzyme is diffused from the lower reagent layer into the upper substrate layer after the sample solution has been spotted. Even when the non-diffusible substrate happens to contain extraneously such an insoluble macromolecular substrate as is not retained in the substrate layer but is migrated into the reagent layer because of an unduly low polymerization degree or an unduly small particle diameter, this insoluble macromolecular substrate will not react with the fragmenting enzyme in the reagent layer.

When an α-amylase is used as the enzyme of an enzyme-labelled antibody (or antigen) and a glucoamylase or an α-glucosidase which will be specifically described herein below is used as the fragmenting enzyme, such an insoluble polysaccharide as the starch having the non-reducing terminal glucose thereof modified with a carboxymethyl group may be used. Though this modified substrate can be the substrate of α-amylase, it cannot be the substrate of glucoamylase or α-glucosidase.

The modifying group of the non-reducing terminal glucose is preferred to be a nonreactive functional group which is incapable of affecting the activity of a labelling enzyme or a fragmenting enzyme. It is preferred to be a hydrophilic modifying group for the purpose of exalting the reactivity of the enzyme in the dry assay element. The modifying groups which answer this description include such hydrophilic groups as a carboxylmethyl group, hydroxypropyl group, and hydroxyethyl group. Otherwise, the terminal glucose may be esterified with phosphoric acid, sulfuric acid, or nitric acid.

Otherwise, when the non-reducing terminal glucose is bound with an adjoining glucose unit in a mode of linkage other than α-1,4-glucoside bond (such as, for example, α-1,6 bond or α-1,3-bond) and is positioned at the point of branching of glucose chain, the polysaccharide containing such non-reducing terminal glucose can be used as a non-diffusible substrate contemplated by this invention. Since such an exo-active glucosidase as glucoamylase is generally an enzyme which decomposes the α-1,4 bond or α-1,6 bond of the linear part of sugar chain from the non-reducing terminal into a glucose unit, it is incapable of decomposing the glucoside bond at the point of branching (mainly the α-1,6 bond or α-1,3 bond). It is, therefore, incapable of being hydrolyzed even when the non-reducing terminal glucose is located at the position at which the non-reducing terminal glucose is branched from the sugar chain.

The α-amylase is an endo-active glucosidase which hydrolyzes the α-1,4-glucoside bond of a sugar chain having not less than four glucose units and, therefore, is capable of being hydrolyzed within the molecule of a substrate irrespectively of the presence or absence of a modification for the terminal glucose or the presence or absence of a branched sugar chain.

By restrictively decomposing the carboxylmethylated starch having a carboxymethyl group incorporated in the glucose unit halfway along the length of a sugar chain from the non-reducing terminal glucose site through the carboxylmethyl modified glucose unit site by the exo-active glucosidase, for example, it is made possible to convert the starch into a substrate having the non-reducing terminal glucose thereof modified with the carboxymethyl group. As concrete examples of the exo-active glucosidase which is used herein, glucoamylase and α-glucosidase may be cited.

The carboxylmethylated starch having the degree of carboxylmethylation thereof exalted by restrictively decomposing the terminal glucose as described above, when used in a dry assay element, has the reactivity thereof augmented with such an endo-active enzyme as α-amylase. This fact is a novel knowledge acquired by the present inventors as will be demonstrated in the working examples to be cited herein below. Although it has not been clarified the reason why the enzymatic activity of the labelling enzyme against an insoluble polysaccharide such as starch is increased by the increase of the degree of carboxylmethylation (the ratio of incorporation) thereof. However, it is estimated that the reactivity of the substrate to the enzyme is improved for the following reason.

The carboxylmethyl group is a hydrophilic group. The rise of the ratio of incorporation of this functional group, therefore, enables the insoluble polysaccharide to acquire a heightened ability to hydrate and become readily wettable in an aqueous solvent. The reaction in a dry assay element is effected by having a sample solution of a minute amount (generally not more than 100 μL) supplied by spotting thereon and the amount of water to be supplied is extremely small. Further, since the water (sample solution) to be supplied is spread in a pertinent layer and immediately migrated to adjoining layers as well, the interior of the pertinent layer which forms the field of the enzymatic reaction turns out to be an environment having an extremely limited water supply. In the layer which has such a limited water supply as mentioned above, the substrate is not allowed to swell amply and react with an enzyme sufficiently. When the degree of swelling of the substrate is increased, even if only slightly, the environment under such a harsh restriction yields to a microscopic structural change and tends to expose a reaction site of the substrate to the enzyme. This is suspected to result in exalting the reactivity of the insoluble polysaccharide with the enzyme in the dry assay element and increasing the sensitivity thereof.

In contrast, when the substrate is caused to react with an enzyme in an aqueous solution, the substrate has already swelled amply and has secured the reactivity with the enzyme. This situation may be logically explained by a supposition that in the environment having an ample water supply, the substrate is capable of swelling amply enough for the reaction and the reactivity thereof with an enzyme is not exalted any further even when the degree of swelling is heightened more or less by increasing the degree of carboxylmethylation of the substrate and consequently enhancing the hydrophilicity thereof.

Fragmenting Enzyme

The fragmenting enzyme may be an enzyme of the same kind as of the labelling enzyme. In such a case, it is preferred that the labelling enzyme is an endo-active enzyme which fragments the molecule intramolecularly to produce an oligomer, and that the fragmenting enzyme is exo-active and acts at the terminal of the molecule to produce a monomer. For instance, when the non-diffusible substrate is a polymer (e.g., starch), a fragmenting enzyme for decomposing the diffusible oligomer (e.g., maltose) produced by the action of the labelling enzyme to a monomer (e.g., glucose) is used. Examples of the fragmenting enzyme include hydrolases for saccharides, specific examples being α-amylase, β-amylase, glucoamylase and α-glucosidase.

When carboxymethyl cellulose is used as the non-diffusible substrate and cellulase is used as the labelling enzyme, C1 enzyme may be used as the fragmenting enzyme. Likewise, when the combination of galactan and galactanase is used, β-galactosidase may be used as the fragmenting enzyme; and when the combination of RNA and ribonuclease is used, exoribonuclease may be used as the fragmenting enzyme.

The combination of the labelling enzyme, the non-diffusible substrate and the fragmenting enzyme can be selected from the enzymes and substrates disclosed in prior literature (for example, "Enzyme Handbook" (compiled under supervision of Bunji Maruo and Nobuo Tamiya and published by Asakura Shoten in 1982) and "Biochemical Handbook" (edited by Nobumasa Imura et al. and published by Maruzen Co., Ltd. in 1984).

Detection System of Lower Molecular Weight Product

The lower molecular weight product produced by fragmentation in the reagent layer by the action of the fragmenting enzyme may be optically detected by using a known detection reagent.

Any known methods may be employed for detecting the final glucose which is formed by the action of the aforementioned fragmenting enzyme. Examples include:

(1) a method in which hydrogen peroxide formed by the oxidation of glucose in the presence of glucose oxidase is detected for example;

(1-1) the method wherein a Trinder reagent is used, as described in Ann. Clin. Biochem., 6, 24 (1964) and J. Clin. Pathol., 22, 246 (1969);

(1-2) the method wherein a Trinder reagent is used, as described in Unexamined Japanese Patent Publication No. 50991/1974 (corresponding to U.S. Pat. No. 3,886,045), U.S. Pat. No. 3,992,158 and Unexamined Japanese Patent Publication No. 164356/1980 (corresponding to U.S. Pat. No. 4,292,272);

(1-3) the method wherein a reagent containing a triaryl-substituted imidazole leuco dye is used, as described in Unexamined Japanese Patent Publication No. 26188/1978 (corresponding to U.S. Pat. No. 4,089,747) and Unexamined Japanese Patent Publication No. 45557/1983 (Chemical Abstracts, 99, (1983): 209284j);

(1-4) the method wherein a reagent containing an imidazole leuco dye substituted with a diarylmonoalkyl, as described in Unexamined Japanese Patent Publication Nos. 193352/1984 (corresponding to EP 0122641A) and 224677/1985 (corresponding to U.S. Pat. No. 4,665,023));

(2) a method wherein NADH produced in the presence of glucose dehydrogenase and NAD is detected; and (3) a method wherein glucose-6-phosphate produced in the presence of hexokinase is detected.

Among these detection methods, the most preferred is the method wherein glucose is oxidized in the presence of glucose oxidase to form hydrogen peroxide which is detected using peroxidase and a leuco dye because of its high detection sensitivity.

These detection reagents may be contained in the reagent layer 12 together with the fragmenting enzyme, or may be contained in another layer disposed below the reagent layer 12 (for example in a second reagent layer or a detection layer) to detect the lower molecular weight product produced. When a leuco dye is used, it is preferred that the dye is dispersed in the hydrophilic binder in the solution in a water-immiscible solvent in consideration of the stability of the formed dye.

Layer Structure of the Analysis Element

The dry immunoassay element of this invention may have a layer structure similar to those of various dry analysis element. The element may be of a multi-layered construction including, in addition to the substrate layer and the reagent layer, a support, a spreading layer, a detection layer, a light-shielding layer, an adhesive layer, a water-absorbing layer, an undercoating layer and so on. Examples of such analysis elements are disclosed in the specifications of Unexamined Japanese Patent Publication Nos. 53888/1974 (corresponding to U.S. Pat. No. 3,992,158), 40191/1976 (corresponding to U.S. Pat. No. 4,042,353), 164356/1980 (corresponding to U.S. Pat. No. 4,292,272) and 4959/1986 (corresponding to European Patent No. 0166365A).

When a light-transmitting and water-impermeable support is used, the dry immunoassay element having the following construction may be used, although the present invention is not limited to the following constructions.

(1) A reagent layer disposed on a support, and a substrate layer superposed on the reagent layer;

(2) A reagent layer disposed on a support, an adhesive layer superposed on the reagent layer and a substrate layer superposed on the adhesive layer in this order;

(3) A support, and a detection layer, a reagent layer and a substrate layer superposed in this order;

(4) A support, and a reagent layer, a light-shielding layer, and a substrate layer superposed in this order;

(5) A support, and a detection layer, a reagent layer, light-shielding layer and a substrate layer superposed in this order;

(6) A support, and a detection layer, a light-reflecting layer, a reagent layer and a substrate layer superposed in this order;

(7) A support, and a second reagent layer, a light-reflecting layer, a first reagent layer and a substrate layer superposed in this order; and (8) A support, and a detection layer, a second reagent layer, a light-reflecting layer, a first reagent layer and a substrate layer superposed in this order.

In the constructions (1) to (6), the reagent layer may be composed of plural layers. The reagent layer may be an immunological reaction layer which contains a component capable of taking part in a immunological reaction as will be described hereinafter.

A water-absorbing layer may be disposed between the support and the reagent or detection layer. Filtering layers may be interposed between the adjacent layers. A spreading layer may be disposed on the substrate layer, or the substrate layer may serve also as a spreading layer.

Substrate Layer

The substrate layer 14 is composed of a water-permeable layer and contains a non-diffusible substrate which is a substrate for the enzyme labelling the antibody.

In order to ensure water-permeability of the substrate layer, it is preferable that the substrate layer is composed of a porous medium or a layer composed of a hydrophilic polymer binder.

The porous layer may be fibrous or non-fibrous. As the fibrous material, filter paper, non-woven cloth, woven cloth (e.g. plain woven cloth), knitted cloth (e.g. tricot knitted cloth) or filter paper made of glass fibers may be used. Examples of the non-fibrous material include a membrane filter composed of cellulose acetate described in Unexamined Japanese Patent Publication No. 53888/1974 (corresponding to U.S. Pat. No. 3,992,258), and a particulate structure layer containing inter connected voids and composed of inorganic or organic fine particles as disclosed in Unexamined Japanese Patent Publication Nos. 53888/1974 (corresponding to U.S. Pat. No. 3,992,258), 90859/1980 (corresponding to U.S. Pat. No. 4,258,001) and 70163/1983 (corresponding to U.S. Pat. No. 4,486,537). A laminated structure made of partially bonded multiple porous layers may also be preferably used, examples of such structure being disclosed in Unexamined Japanese Patent Publication Nos. 4549/1986 (corresponding to EP 0166265A), 116258/1987 (Chemical Abstracts, 108, (1988): 3041y), 138756/1987 (EP 0226465A), 138757/1987 (EP 0226465A) and 138758/1987 (EP 0226465A).

The porous layer may be a spreading layer having a so-called metering function to spread a liquid over an area substantially in proportion to the volume of the liquid fed thereto. Preferable materials for the spreading layer are woven and knitted fabrics. The woven fabrics or like may be subjected to the glow discharge treatment as described in Unexamined Japanese Patent Publication No. 66359/1982 (corresponding to GB 2,087,974A and U.S. Pat. No. 4,783,315). In order to adjust the area or rate for spreading, the spreading layer may contain a hydrophilic polymer or a surfactant as described in Unexamined Japanese Patent Publication Nos. 222770-1985 (corresponding to EP 0162301A), 219397/1988 (corresponding to DE 37 17 913 A), 112999/1988 (corresponding to DE 37 17 913A) and 182652/1987 (corresponding to DE 37 17 913A).

One convenient method is a method wherein the substrate is impregnated into or coated on a porous membrane made of, for example, paper, cloth or a high polymer, and then the composite is applied on another water-permeable layer, for example, a reagent layer superposed on the support by a method as described in Unexamined Japanese Patent Publication No. 164356/1980 (corresponding to U.S. Pat. No. 4,292,272). A further method comprises the steps of bonding a porous layer on another water-permeable layer (for example a reagent layer) by a method as described above, and coating a composition containing the substrate on the porous layer. Any known methods may be employed for the impregnation or coating on the porous layer. Coating may be effected by selecting a suitable method, for example, dip coating, doctor coating, hopper coating and curtain coating.

Although the thickness of the substrate layer made by any of the aforementioned methods is not limited, the thickness may range within 1 μm to 50 μm and preferably, from 2 μm to 30 mm, when the layer is provided as a coating layer. When it is provided by another method, for example by piling of a laminate, the thickness thereof may be varied within a wide range of from several tens of μm to several hundreds of μm.

The substrate layer may be a water-permeable layer composed of a hydrophilic polymer binder, such as, gelatin and derivatives thereof (e.g. phthalated gelatin), derivatives of cellulose (e.g. hydroxyethyl cellulose), agarose, sodium alginate, acrylamide copolymers, methacrylamide copolymers, copolymers of acryl amides or methacrylamides with various vinyl monomers, polyhydroxyethyl methacrylate, polyvinyl alcohol, polyvinyl pyrrolidone, sodium polyacrylate, and copolymers of acrylic acid with various vinyl monomers.

The substrate layer composed of a hydrophilic polymer binder may be provided by coating an aqueous solution or dispersion of the substrate, an additional other reagent composition and a hydrophilic polymer binder on another layer, such as a support or a detection layer, and then drying the coated solution or dispersion, as disclosed in the specifications of Japanese Patent Publication No. 21677/1978 (corresponding to U.S. Pat. No. 3,992,158), Unexamined Japanese Patent Publication Nos. 164356/1980 (corresponding to U.S. Pat. No. 4,292,272), 101398/1979 (corresponding to U.S. Pat. No. 4,132,528), and 292063/1986 (Chemical Abstracts, 106, (1987): 210567y). The thickness of the dried substrate layer containing a hydrophilic polymer as the binder may range from about 2 µm to about 50 µm, and preferably, from about 4 µm to about 30 µm, and the coverage thereof may range from about 2 g/m.sup.2 to about 50 g/m.sup.2, and preferably, from about 4 g/m.sup.2 to about 30 g/m.sup.2.

To improve the characteristics, such as, coating characteristics, diffusibility of the diffusible material, reactivity and storage stability, the substrate layer may include, in addition to the non-diffusible substrate, various organic or inorganic additives, for example, enzyme activators, coenzymes, surfactants, pH buffer reagents, fine particles, antioxidants, etc. Examples of buffer system, which may be contained in the substrate layer, include pH buffer reagents as described in "KAGAKU BINRAN, KISOHEN" edited by Japanese Chemical Society (MARUZEN, Tokyo, 1966), pp 1312-1320; R. M. C. Dawson et al., "Data for Biological Research", $2^{nd}$ Edition (Oxford at the Clarendon Press, 1969), pp 476-508; "Biochemistry", 5, pp 467-477 (1966); and "Analytical Biochemistry", 104, pp 300-310 (1980). Specific examples of usable buffers are buffer reagents containing tris(hydroxymethyl)aminomethane (Tris), buffer reagents containing phosphates, buffer solutions containing borates, buffer reagents containing citric acid or citrates, buffer reagents containing glycine, buffer solutions containing Bicine, and buffer reagents containing HEPES.

Reagent Layer

The reagent layer 12 contains a reagent composition for detecting the diffusible material which has diffused and migrated from the substrate layer 14. As desired, a fragmenting enzyme may be contained in the detection reagent composition and a detection reagent composition for detecting the lower molecular weight product formed by the action of the fragmenting enzyme may also be contained.

The reagent layer 12 is composed of a water-permeable layer which is preferably a continuous layer made of a hydrophilic polymer binder, similar to the water-permeable layers as described in the description of the substrate layer. The used hydrophilic polymer binder may be determined in consideration of the diffusible product formed in the substrate layer and the coloring reagent contained in the reagent layer.

Support

The support 10 may be light-nontransmitting (opaque), light-semi-transmitting (translucent) or light-transmitting (transparent), and it is generally preferable that the support is light-transmitting and water-impermeable. Preferable materials for the light-transmitting and water-impermeable support are polyethylene terephthalate and polystyrene. In general, an undercoating is provided or the support is subjected to hydrophilization treatment in order to firmly adhere the hydrophilic layer.

Immunological Reaction Layer

The substrate layer 14 shown in FIG. 1 may contain enzyme-labelled or unlabelled immunological binding partner (antigen or antibody), in addition to the diffusible substrate, to form an immunological reaction layer in which an immunological reaction takes place.

For example, the substrate layer is made to contain therein
(1) an enzyme-labelled antibody when the amount of an antigen subjected to the assay is determined by causing the antigen to react with the enzyme-labelled antibody;
(2) an antibody and an enzyme-labelled antigen when the amount of an antigen subjected to the assay is determined by causing the antigen to react with an antibody and the enzyme-labelled antigen;
(3) a polymerized antigen and an enzyme-labelled antibody when the amount of an antigen subjected to the assay is determined by causing the antigen to react with the polymerized antigen and the enzyme-labelled antibody;
(4) an enzyme-labelled antigen when the amount of an antibody subjected to the assay is determined by causing the antibody to react with the enzyme-labelled antigen; or
(5) an antigen and an enzyme-labelled antibody when the amount of an antibody subjected to the assay is determined by causing the antibody to react with the antigen and the enzyme marker antibody.

With such constructions, the substrate layer functions as an immunological reaction layer for allowing an immunological reaction to proceed additionally therein. In this case, a homogeneous enzyme immunological reaction takes place in the element only by spotting a sample solution on the element.

Alternatively, either of a given pair of reactants may be contained in the substrate layer and the remainder in a water-permeating layer superposed on the substrate layer. Otherwise, a water-permeating layer formed of one layer or a plurality of layers may be formed on the substrate layer and these layers may be allowed to contain immunological binding partners necessary for an immunological reaction. The stratal construction of these immunological reaction layers can be arbitrarily decided, depending on the mode of the immunological reaction wished to be effected.

Figure 2:
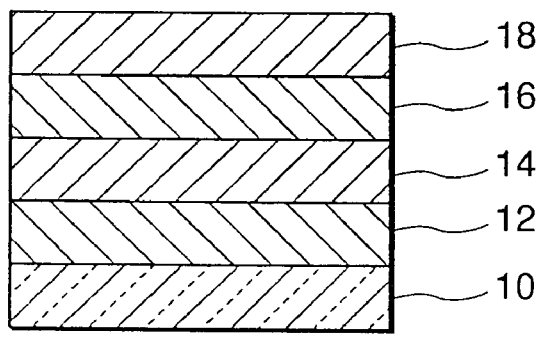
FIG. 2 is an illustration showing another embodiment of the immunoassay element of the present invention.

In the case of the reaction of (2) mentioned above, for example, the antibody and the enzyme-labelled antigen may be severally contained in a plurality of layers other than the substrate layer. For example, the immunoassay element may comprise a water-permeable layer 16 containing an antigen and superposed on the substrate layer 14 and further comprise thereon a water-permeable layer 18 containing an enzyme-labelled antigen as illustrated in FIG. 2. In this case, the antigen (ligand) in the sample diffuses and permeates through the layer 16 together with the enzyme-labelled antigen of the layer 18. In the layer 16, the antigen and the enzyme-labelled antigen are respectively bound with the antibody and further allowed to migrate into the substrate layer 14.

Conversely, the immunoassay element may comprise the water-permeable layer 16 containing the enzyme-labelled antigen; and the water-permeable layer 18 superposed on the layer 18 and containing the antibody. In this case, the antigen (ligand) in the sample binds with the antibody contained in layer 18, and then migrates into the layer 16. In the layer 16, the antibody which has escaped being bound with the antigen binds with the enzyme-labelled antigen, and further migrates into the substrate layer 14.

Figure 3:
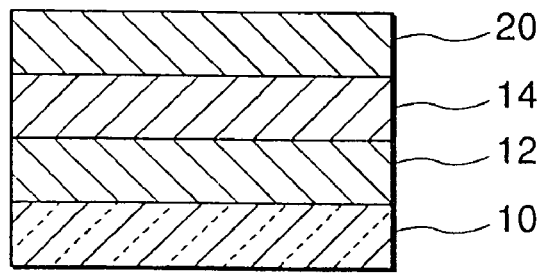
FIG. 3 is an illustration showing yet another preferred embodiment of the immunoassay element of the present invention.

Optionally, one layer other than the substrate layer may contain the antibody and the enzyme-labelled antigen together in a substantially dry state or in the substantial absence of water. For example, an immunoassay element may be constructed by forming on the substrate layer 14 a water-permeable layer 20 containing the antibody and the enzyme-labelled antigen together in a substantially dry state or in the substantial absence of water as illustrated in FIG. 3. In this case, when the sample using water as the solvent therefor is supplied on the layer 20, the ligand (antigen) in the sample and the enzyme-labelled antigen are bound respectively with the antibody in the water originating from the sample in the layer 20, and then migrates into the substrate layer 14. In order to contain an antibody and an enzyme-labelled ligand together in a separate layer in the substantially dry state or in a substantial absence of water, either or both of the antibody and the enzyme-labelled antigen may be dissolved or dispersed in a non-aqueous solvent such as an alcohol (for example, ethanol) and then the resultant solution or dispersion is impregnated in the water-permeable layer.

When the provision of an immunoreaction layer is omitted, the assay element of this invention can be used also for assaying an enzyme capable of decomposing the non-diffusible substrate contained in the substrate layer 14. When carboxylmethylated starch, starch, amylose or amylopectin is used as the non-diffusible substrate, for example, the assay element of this invention can be used for the assay of an endo-active glucosidase such as α-amylase or β-amylase.

Process for Preparing the Immunoassay Element

The dry immunoassay element of the invention may be prepared by any of the known processes described in the specifications of aforequoted patents.

The analysis element of the invention may be cut into a square piece having sides each ranging from about 15 mm to about 30 mm or a disk having a substantially the same area. It is preferred, in view of the preparation, packaging, shipping, storage and measuring operations, that the element be contained in a slide frame as disclosed, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent Publication No. 63452/1982, Unexamined Japanese Utility Model Publication No. 32350/1983 and Unexamined Japanese Patent Publication No. 501144/1983 (corresponding to International Publication WO 83/00391) for use as a slide for chemical analysis. For the convenience in some uses, it may be formed in a tape shape which is contained in a cassette or magazine, or a small piece thereof may be applied on or contained in a card having an opening.

Analyzing Method Using the Immunoassay Element

The analysis element of the invention may be used for the quantitative analysis of an analyte ligand (or an analyte antibody) in a sample liquid by using it through the operations described in the specification of the aforequoted patents.

For example, about 5 μL to about 30 μL, preferably 8 μL to 15 μL of an aqueous sample liquid, such as, serum, plasma or urine, is spotted or otherwise fed on the substrate layer 14. The analysis element spotted with the sample liquid is then incubated at a constant temperature of from about 20° C. to about 45° C., preferably at a constant temperature of from about 30° C. to about 40° C., for 1 to 10 minutes. The reflection optical density of the color or the change in color in the element may be measured from the light-transmitting support side, and the quantity of the ligand (or antibody) contained in the sample can be determined using a preliminarily prepared calibration curve based on the principle of colorimetry. The volume of the spotted liquid sample and the time and temperature for incubation are maintained constant to improve the accuracy in quantitative analysis.

The measuring operation may be carried out while using the chemical analysis apparatus described in Unexamined Japanese Patent Publication Nos. 125543/1985, 220862/1965, 294367/1986 and 161867/1983 (the last-mentioned Publication corresponding to U.S. Pat. No. 4,424,191) to realize a quantitative analysis at a high accuracy by extremely easy operations. Meantime, a semi-quantitative analysis may be conducted by judging the degree of coloring by naked eye if such visual judgment is adequate for the object or required accuracy.

When the analysis element has no immunological reaction layer, namely when the analysis element does not contain therein an immunological binding partner necessary for the immunological reaction with an antigen or antibody to be analyzed, a necessary immunological reaction can be carried out in a proper reaction mixture other than the assay element, and then the resultant reaction mixture is spotted on the element. Thus the analyte can be analyzed as a change of the enzymatic activity of the labelling enzyme. For assaying an antigen, for example, an aqueous sample solution is mixed with a solution containing an antibody and an enzyme-labelled ligand to complete the binding reaction, and then spotted on the substrate layer.

EXAMPLE 1

Preparation of Endo Type Specific Reactive Substrate

10 Gram of carboxylmethylated starch made by Edward Mendel Company Inc. and sold under a trademark designation of "Exprotab" was dispersed in 1 liter of 0.1 M borate buffer solution (pH 10), and then stirred for one hour. The resultant dispersion was adjusted with hydrochloric acid and phosphoric acid to pH 5.5, and then 1000 U of glucoamylase (made by Toyobo K.K.) was added to react with the carboxylmethylated starch at 37.degree. C. for 16 hours. After the completion of the reaction, the reaction mixture was subjected to high-speed centrifugation at about 10,000 G. This purification by centrifugation was repeated until the electro-conductivity of the separated supernatant fell below 20 μS/cm to remove the soluble components. Then, 10 liters of ethanol was added to the resultant dispersion while stirring the latter sufficiently. The white precipitate which consequently occurred was collected by filtration under suction pressure. It was dried at 30.degree. C. for 10 hours to obtain 5.2 g (yield: 52%) of carboxylmethylated starch, which is specific to an endo-type enzymatic reaction.

EXAMPLE 2

A reagent solution containing a cross-linking reagent was coated on a colorless and transparent polyethylene terephthalate (PET) sheet (support) coated with a gelatin undercoating and having a thickness of 180 μm. The sheet was then dried, forming a reagent layer wherein the respective components had the coverages as set forth below.

| | |
|---|---|
| Alkaline-treated Gelatin | 14.5 g/m$^2$ |
| Nonylphenoxypolyethoxyethanol | 0.2 g/m$^2$ |
| (Containint 9 to 10 (average) of Oxyethylene Unites) | |
| Glucose oxidase | 5,000 U/m$^2$ |
| Peroxidase | 15,000 U/m$^2$ |

-continued

| | |
|---|---|
| Glucoamylase | 5,000 U/m² |
| 2-(4-hydroxy-3,5-dimethoxyphenyl)-4-[4-(dimethylamino)phenyl]-5-phenethyl-imidazole (Leuco Dye) Acetate | 0.38 g/m² |
| Bis[(vinylsulfonylmethylcarbonyl)amino]-methane | 0.1 g/m² |

An adhesive layer was coated on the reagent layer to have the following coverage, and then dried.

| | |
|---|---|
| Alkaline-treated Gelatin | 14.5 g/m² |
| Bis[(vinylsulfonylmethylcarbonyl)amino]-methane | 0.1 g/m² |

Then, an aqueous solution containing the following reagent was coated over the surface of the reagent layer to have the following coverages to swell the gelatin layer and a tricot knitted cloth made by knitting PET spun yarn of 36 gage corresponding to 50 deniers and having a thickness of about 250 μm was then laminated thereon, by pressing with a uniform light pressure to form a porous spreading layer.

| | |
|---|---|
| Nonylphenoxypolyethoxyethanol (Containing 9 to 10 (average) of Oxyethylene Units) | 0.15 g/m² |
| Bis[(vinylsulfonylmethylcarbonyl)amino]-methane | 0.4 g/m² |

Thereafter, a substrate layer was formed by coating carboxylmethylated starch specific to an endo-type enzymatic reaction prepared by Example 1, followed by drying, to have the following coverages, to prepare a multi-layered analysis element for the quantitative analysis of CRP.

| | |
|---|---|
| Carboxylmethylated starch | 3.5 g/m² |
| Mannitol | 3.0 g/m² |
| MES (2-morpholinoethane sulfonic acid) | 2.0 g/m² |

The thus prepared element was cut into rectangular chips, 14 mm.times.13 mm. The chips were severally encased with slide frames described in JP-A-57-63,452 to prepare multi-layered dry slide 1 for the analysis of CRP according to the present example.

As a comparative example, a control slide 2 having the same construction as the slides 1 of the example except that an untreated carboxylmethylated starch (Exprotab) was used as a substrate in the place of the carboxylmethylated starch specific to the endo-type enzymatic reaction.

EXAMPLE 3

Figure 4:
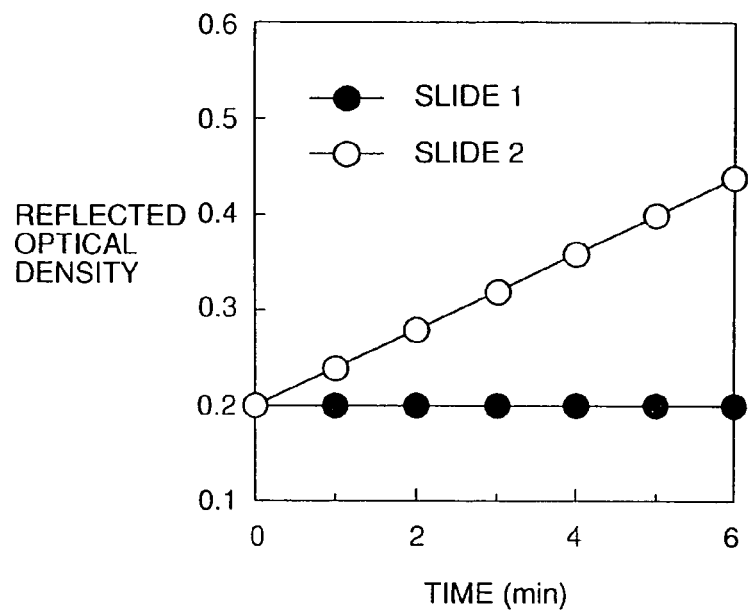
FIG. 4 is a diagram showing the results of Example 4, i.e., a diagram showing the time-course changes in reflected optical density obtained when a buffer solution containing no labelling enzyme was supplied by spotting on the immunoassay element on a Slide 1 (working example) and a Slide 2 (comparative example)

The 50 mM glycerophosphate buffer solution (pH 7) was spotted in a unit amount of 10 μL severally on the dry slides 1 of Example 2 and the dry slides 2 of Comparative Example. Thereafter, the slides were kept at 37° C. and measured from the PET supporting member side for reflected optical density at a central wavelength of 650 nm along the course of time. The time-course changes of the reflected optical density after the buffer-spotting in the are shown in FIG. 4.

On the control slides 2 of Comparative Example which used untreated carboxylmethylated starch as a non-diffusible substrate, the reflected optical density was found to begin increasing along the course of time after the spotting of the buffer solution (indicated by the mark -○- in the diagram). This fact indicates that the untreated carboxylmethylated starch was decomposed into glucose by the glucoamylase (fragmenting enzyme), an exo-active enzyme, migrated from the reagent layer.

In contrast, on the slides 1 of Example 2 which used carboxylmethylated starch rendered specific to an endo-type enzymatic reaction in advance by the treatment with glucoamylase, the reflected optical density was constant and showed no increase (as indicated by the mark -●- in the diagram).

EXAMPLE 4

Figure 5:
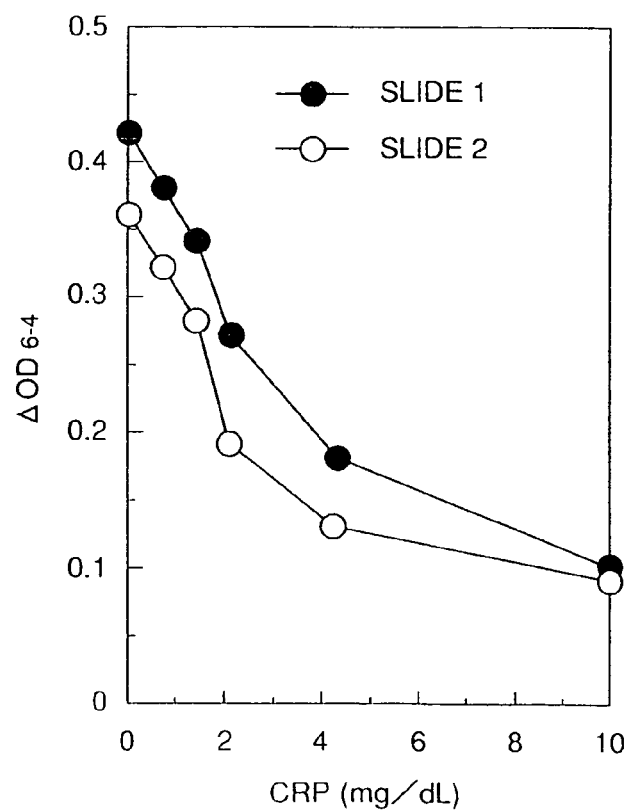
FIG. 5 is a diagram showing the results of Example 4, i.e., a diagram showing the calibration curves of immunoassay element on the Slide 1 (working example) and the Slide 2 (comparative example)

10 μl for each of the 50 mM glycerophosphate buffer solution (pH 7) containing an amylase-labelled anti-CRP-IgG (0.1 mg/mL) and a known amount of CRP was spotted on the dry slides 1 of Example 2 and the dry slides 2 of Comparative Example. The slides 1 and 2 were maintained at 37° C. and measured from the PET support side for reflected optical density with a visible light having a central wavelength of 650 nm. The differences in reflected optical density ($\Delta OD_{6-4}$) between 4 minutes and 6 minutes after the spotting are shown in FIG. 5. It is clear from the calibration curve of FIG. 5 that the dry immunoassay element of this invention using a carboxylmethylated starch rendered specific in advance to the endo-type enzymatic reaction was capable of determining the amount of CRP with high accuracy (as indicated by the mark -●- in the diagram). The changes of $\Delta OD_{6-4}$ relative to the change of CRP concentration were large as compared with those of the Comparative Example (as indicated by the mark -○- in the diagram), indicating an improvement in sensitivity.

EXAMPLE 5

A multi-layered analysis element having the same construction as the element of Example 2 was prepared by faithfully repeating the procedure of Example 2. On the tricot knitted cloth layer, which served both as a substrate layer and a spreading layer, an ethanol solution of the amylase-labelled CRP-IgG was coated and impregnated to have a coverage of 3 mg/m², followed by drying, to prepare a multi-layered immunoassay slide 3 for analysis of CRP (Example 5). As a Comparative Example, the tricot knitted cloth layer of the multi-layered assay element of the comparative slide 2 prepared in Example 2 was similarly coated and impregnated with an ethanol solution of the amylase-labelled CRP-IgG at a coverage of 3 mg/m², and then dried to prepare a comparative multi-layered immunoassay slide 4.

EXAMPLE 6

Figure 6:
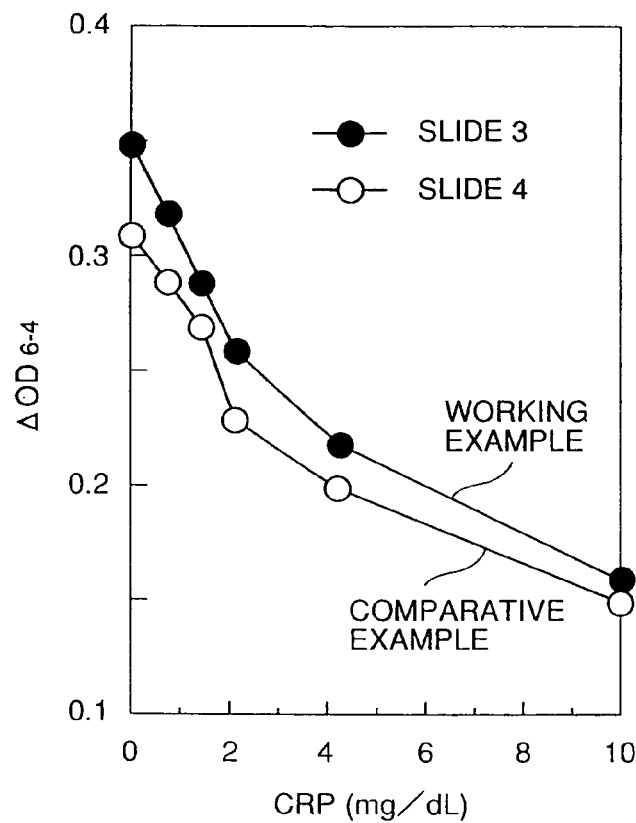
FIG. 6 is a diagram showing the results of Example 6, i.e., a diagram showing the calibration curves of the immunoassay element for CRP analysis, the Slide 3 being the working example and the Slide 4 being the comparative example.

On the slides 3 and slides 4, 10 μl for each of 50 mM glycerophosphate buffer solution (pH 7) containing CRP in a varying concentration was spotted. The slides were maintained at 37° C. and measured from the support side for reflected optical density at a wavelength of 650 nm to find differences in reflected optical density ($\Delta OD_{6-4}$) between 4 minutes and 6 minutes after the spotting of the solution. It is clear from the calibration curve of FIG. 6 that the dry immunoassay element of this invention using the carboxylmethylated starch specific to the endo-type reaction (as indicated by the mark -●- in FIG. 6) was capable of performing quantitative assay of CRP with high sensitivity as compared with the comparative example (as indicated by the mark -○-).

EXAMPLE 7

The slides 3 of Example 5 and the slides 4 of the comparative example were studied comparatively for reproducibility (CV). On the slides 3 and slides 4, four samples (L-1, L-2, M, and H) of a CRP-containing human standard blood serum were spotted in a unit amount of 10 μL. The slides were maintained at 37° C. and measured from the supporting member side for reflected optical density at a wavelength of 650 nm to find differences in reflected optical density ($\Delta OD_{6-4}$) between 4 minutes and 6 minutes after the spotting of the solution. A calibration curve for the slides 3 of Example 5 and a calibration curve for the slides 4 of comparative example were separately prepared in advance. From the values of $\Delta OD_{6-4}$ of the samples consequently found, the relevant CRP concentration (measured values) were calculated. This measurement was performed on each of the samples up to 10 repetitions. The averages, standard deviations (S.D.), and coefficient of variation (CV=(S.D./Aberage)×100) of the results of measurement were consequently obtained. The results are shown in Tables 1 and 2 given below.

TABLE 1

Reproducibility of Slides 3 (Example 5)

| | Sample | | | |
|---|---|---|---|---|
| | L-1 | L-2 | M | H |
| Measured | 2.3 | 1.7 | 5.3 | 9.0 |
| Value | 2.6 | 1.6 | 5.4 | 8.7 |
| (mg/dL) | 2.4 | 1.4 | 5.3 | 9.0 |
| | 2.4 | 1.5 | 5.1 | 9.4 |
| | 2.2 | 1.5 | 5.0 | 9.2 |
| | 2.1 | 1.5 | 5.3 | 8.7 |
| | 2.4 | 1.6 | 5.3 | 8.9 |
| | 2.3 | 1.5 | 5.9 | 9.2 |
| | 2.2 | 1.5 | 5.6 | 9.1 |
| | 2.2 | 1.6 | 5.5 | 9.5 |
| Average | 2.3 | 1.5 | 5.4 | 9.1 |
| S.D. | 0.1 | 0.1 | 0.3 | 0.3 |
| CV | 6.4 | 5.3 | 4.9 | 3.0 |

TABLE 2

Reproducibility of Slides 4 (Comparative Example)

| | Sample | | | |
|---|---|---|---|---|
| | L-1 | L-2 | M | H |
| Measured | 2.5 | 1.1 | 5.8 | 10.6 |
| Value | 2.7 | 1.9 | 6.1 | 10.4 |
| (mg/dL) | 2.0 | 1.9 | 6.2 | 9.7 |
| | 2.2 | 1.9 | 5.6 | 10.3 |
| | 2.1 | 1.9 | 5.3 | 10.4 |
| | 2.9 | 2.2 | 5.9 | 12.1 |
| | 3.3 | 2.3 | 5.4 | 12.9 |
| | 3.1 | 2.1 | 5.8 | 11.2 |
| | 2.1 | 2.3 | 5.8 | 12.4 |
| | 2.3 | 1.9 | 5.9 | 13.6 |
| Average | 2.5 | 1.9 | 5.8 | 11.4 |
| S.D. | 0.5 | 0.3 | 0.3 | 1.3 |
| CV | 18.9 | 17.4 | 4.8 | 11.5 |

It is noted from Tables 1 and 2 that the slides 3 of Example 5 of this invention using the substrates specific to the endo-type reaction showed only slight variation and excelled in reproducibility, whereas the conventional slides 4 for comparison showed a wide variation of measured value (concentration). Particularly, in the low concentration range (samples L-1 and L-2) and the high concentration range (sample H), the CV values of the slides 3 of working example were about ⅓ lower than those of the slides 4 for comparison, indicating that the immunoassay elements according to the present invention excelled in reproducibility and in accuracy as well.

EXAMPLE 8

The slides 3 of Example 5 and the slides 4 for comparison were studied comparatively for stability of preservation. Since the dry assay elements are generally stable for a duration of about one month. In the present example, therefore, the slides were preserved at 25° C. by way of acceleration of test and the values of measurement obtained one day, three days, and seven days after manufacture of slide were compared with the values of measurement obtained immediately (0 day) after manufacture of slide. On the slides 3 (Example 5) and the slides 4 (comparison) after specified numbers of days following manufacture of slide, a CRP-containing standard samples CP1 (1.4 mg/dL), CP2 (4.2 mg/dL), and CP3 (10.0 mg/dL) were severally spotted in a unit amount of 10 μL. These slides were maintained at 37° C. and measured from the supporting member side for reflected optical density at a wavelength of 650 nm to find the differences in reflected optical density ($\Delta OD_{6-4}$) between 4 minutes and 6 minutes after the deposition of the solution in the form of a spot. The results are shown in Tables 3 and 4 below.

TABLE 3

Storage Stability of Slides 3 (Example 5)

| | $\Delta OD_{6-4}$ after storage of | | | |
|---|---|---|---|---|
| Slide | 0 day | 1 day | 3 days | 7 days |
| CP1 | 0.3432(100%) | 0.3355(98%) | 0.3339(97%) | 0.3276(96%) |
| CP2 | 0.2734(100%) | 0.2685(98%) | 0.2610(96%) | 0.2658(97%) |
| CP3 | 0.2045(100%) | 0.2065(101%) | 0.2002(98%) | 0.1938(95%) |

TABLE 4

Storage Stability of Slides 4 (Comparative Example)

| | $\Delta OD_{6-4}$ after storage of | | | |
|---|---|---|---|---|
| Slide | 0 day | 1 day | 3 days | 7 days |
| CP1 | 0.3358(100%) | 0.3271(97%) | 0.3171(94%) | 0.2884(86%) |
| CP2 | 0.2536(100%) | 0.2467(97%) | 0.2285(90%) | 0.2138(84%) |
| CP3 | 0.1753(100%) | 0.1656(94%) | 0.1587(91%) | 0.1390(79%) |

On the slides 4 (for comparison) using the conventional untreated carboxylmethylated starch as the substrate, the values of $\Delta OD_{6-4}$ decreased with passage of days of preservation at 25° C., decreases of 5-10% found on the third day and large decreases in the approximate range of 15-20% on the seventh day. In contrast thereto, on the slides 3 (Example 5) using the present invention's carboxylmethylated starch prepared as a substrate specific to the endo-type reaction, the decreases of the value of $\Delta OD_{6-4}$ were only 2-4% on the third day and about 3-5% on the seventh day respectively of preservation.

The results indicate that the immunoassay elements according to the present invention excelled in storage stability.

EXAMPLE 9

Preparation of Endo-Type Selectively Reactive Substrate

In 8,960 g of super-pure water, 453 g of carboxylmethylated starch (made by Edward Mendel Company Inc. and sold under a trademark designation of "Exprotab") was stirred for about 4 hours and swelled. The swelled starch was alkalinized by addition of 1139 g of 0.5N NaOH and stirring for about one hour. Thereafter, it was reverted to pH 7 by the addition of 32 g of acetic acid. It was adjusted to pH 5.7 with an MES (2-morpholinoethane sulfonate) buffer solution and then caused to react with 80 g of glucoamylase enzyme solution (320 k Unit/L, 5 mM MES, pH 6.0, made by Toyobo K.K.) at 37° C. for 12-20 hours. The reaction solution consequently obtained was diluted with pure water to a total volume of 140 L. The resultant suspension was passed through a ceramic membrane filter (monolithic type, 2 μm in pore size and 0.24 m² in membrane area, made by Nippon Gaishi K.K. and sold under a registered trademark of "CEFILT-MF"). The ceramic membrane filter was deprived of a soluble component by circulating pure water through the filter until the electroconductivity of the filtered water fell below 20 μS/cm. The residue of the carboxylmethylated starch was collected from the filter and diluted with purified water to a total volume of 100 L. About 3.6 L of the diluted residue was centrifuged at 7,500 rpm for 10 minutes and the residue of centrifugation was collected. About 18 L of isopropyl alcohol was added to the residue, and the white substance consequently precipitated was collected by filtration under reduced pressure. The procedure from the centrifugation through the precipitation of isopropyl alcohol was performed up to about 26 repetitions and the residues consequently formed in the successive rounds of procedure were gathered and dried at 35° C. for 24 hours. The operation afforded 220 g of glucoamylase-treated carboxylmethylated starch specific to an endo-type enzymatic reaction (hereinafter referred to as "GA-treated CMS").

As a comparative example (Control), a carboxylmethylated starch was prepared by faithfully repeating the operation mentioned above while omitting the treatment with glucoamylase (non-glucoamylase-treated carboxylmethylated starch; hereinafter referred to as "untreated CMS").

EXAMPLE 10

The GA-treated CMS and the untreated CMS obtained in Example 9 were tested for degree of carboxylmethylation and the dispersions thereof in water were tested for degree of swelling. The degree of carboxylmethylation was determined by finding the ratio of glucose unit modified with a carboxylmethyl group to the whole glucose unit by means of $^{13}$C-NMR. The degree of swelling was determined by preparing 10 mL of an aqueous 0.7% solution of a given CMS, placing the aqueous solution in a test tube, allowing it to stand at rest at 25° C. for 30 minutes, and then measuring the volume (mL) of CMS consequently settled to the bottom of the test tube. The volume was reported as the degree of swelling.

It is noted from the results given in Table 5 below that the carboxylmethylated starch treated with the glucoamylase gained in degree of carboxylmethylation and that 28% of the whole glucose units formed therein possessed a carboxylmethyl group. This fact indicates that the treatment with glucoamylase resulted in decreasing the amount of non-CM-modified glucose units in the CM-modified starch and consequently increasing the ratio of the CM-modified glucose units because the treatment hydrolyzed the glucoside bonds from the non-reducing terminal through the point immediately preceding the point of carboxylmethylation. It is also conceivable that the increase in the ratio of incorporation of the carboxylmethyl group, a hydrophilic group, resulted in adding to the ease of hydration and exalting the degree of swelling.

TABLE 5

|  | Untreated CMS | GA-treated CMS |
|---|---|---|
| Degree of Carboxylmethylation | 21% | 28% |
| Degree of swelling | 4.5 | 5.5 |

EXAMPLE 11

Reactivity of GM-Treated CMS with Glucoamylase

The glucoamylase-treated carboxylmethylated starch obtained in Example 9 and the non-glucoamylase-treated carboxylmethylated starch of comparative example were severally dispersed in a 5 mM MES buffer solution (pH 6.0, containing 0.5% of Block Ace (made by Snow Brand Milk Products Co., Ltd.) and 68 μM of $CaCl_2$) to produce 0.2% (W/V) dispersions. To 7 mL of the 0.2% CMS dispersions, 70 μL of glucoamylase solution (made by Toyobo K.K., 320 k Unit/L, 5 mM MES, pH 6.0) was added, and shaken together at 37° C. for 60 minutes at 120 rpm to induce a reaction. The reaction solutions consequently obtained were combined with 70 μL of 10% phosphoric acid and ice cooled to stop the reaction. The resultant reaction solutions were centrifuged at 12,000 rpm for 4 minutes to separate the unaltered CMS. One hundred (100) μL of the supernatant of centrifugation containing the produced glucose was added to 3 mL of a reaction solution A of the following composition and they were together shaken at 37° C. for 30 minutes at 120 rpm to induce a coloring reaction. The resultant reaction solutions were tested for absorbancy at a wavelength of 727 nm. Relevant calibration curves were prepared by adding 100 μL of a glucose solution of known concentration to 3 mL of the reaction solution A and subjecting the resultant mixtures to the same coloring reaction.

| Reaction solution A | |
|---|---|
| Leuco dye (N-(carboxymethylaminocarbonyl)-4,4'-bis(dimethylamino)-diphenylamine sodium salt) (Wako Junyaku K. K. product code; "DA-64") | 3.9 mg |
| Glucose oxidase (Toyobo K. K: product code; "GLO-501") | 139 units |
| Peroxidase (Toyobo K. K. product code; "PEO-301") | 115 units |
| 100 mM MES buffer solution (pH 6.0) | 100 mL |

The measurement was performed on the GA-treated CMS up to five repetitions and on the untreated CMS up to two repetitions. It is noted from the results given in Table 6 that the CM starch not treated with glucoamylase produced about 33 μg of glucose per gram, whereas the CM starch treated in advance with glucoamylase only produced an average of not more than 0.1 μg of glucose. This fact indicates that nearly all the non-reducing terminal glucose of the GA-treated CMS of this invention was either modified or positioned at the point of chain branching and would not form a substrate of glucoamylase, an exo-reactive type enzyme.

TABLE 6

|  | Glucose produced from 1 g of CMS | Average |
|---|---|---|
| GA-treated CMS | 0.25 (μg) | |
|  | 0.07 | |
|  | −0.02 | |
|  | 0.08 | |
|  | 0.08 | 0.09 (μg) |
| Untreated CMS | 33.56 (μg) | |
|  | 33.63 | 33.60 (μg) |

EXAMPLE 12

Reactivity of GA-Treated CMS with α-Amylase (Wet System)

The glucoamylase-treated carboxylmethylated starch obtained in Example 9 and the non-glucoamylase-treated carboxylmethylated starch of comparative example were severally dispersed in a 5 mM MES buffer solution (pH 6.0, containing 0.5% of Block Ace (made by Snow Brand Milk Products Co., Ltd.) and 68 μM of $CaCl_2$) to produce 0.2% (W/V) dispersions. The 0.2% CMS dispersions, 7 mL in volume, and 70 μL of an α-amylase solution of a varying concentration added severally thereto were shaken together at 37° C. for 60 minutes at 120 rpm to induce a reaction. The reaction solutions obtained consequently were combined with 70 μL of 10% phosphoric acid and ice cooled to stop the reaction. The resultant reaction solutions were centrifuged at 12,000 rpm for 4 minutes to effect separation of the unaltered CMS. One hundred (100) μL of the supernatant of centrifugation containing the produced glucose was added to 3 mL of a reaction solution B of the following composition and they were together shaken at 37° C. for 30 minutes at 120 rpm to induce a coloring reaction. The resultant reaction solutions were tested for absorbency at a wavelength of 727 nm. Relevant calibration curves were prepared by adding 100 μL of a glucose solution of known concentration to 3 mL of the reaction solution B and subjecting the resultant mixtures to the same coloring reaction. A graph was obtained by plotting the contents of oligosaccharides formed based on the calibration curves (FIG. 7).

| Reaction solution B | |
|---|---|
| Leuco dye | 3.9 mg |
| (N-(carboxymethylaminocarbonyl)-4,4′-bis(dimethylamino)-diphenylamine sodium salt) (Wako Junyaku K. K; product code: "DA-64") | 3.9 mg |
| Glucoamylase (Toyobo K. K. product code: "GLA-111") | 180 units |
| Glucose oxidase (Toyobo K. K; product code: "GLO-501") | 139 units |
| Peroxidase (Toyobo K. K; product code: "PEI-301") | 115 units |
| 100 mM MES buffer solution (pH 6.0) | 100 mL |

Figure 7:
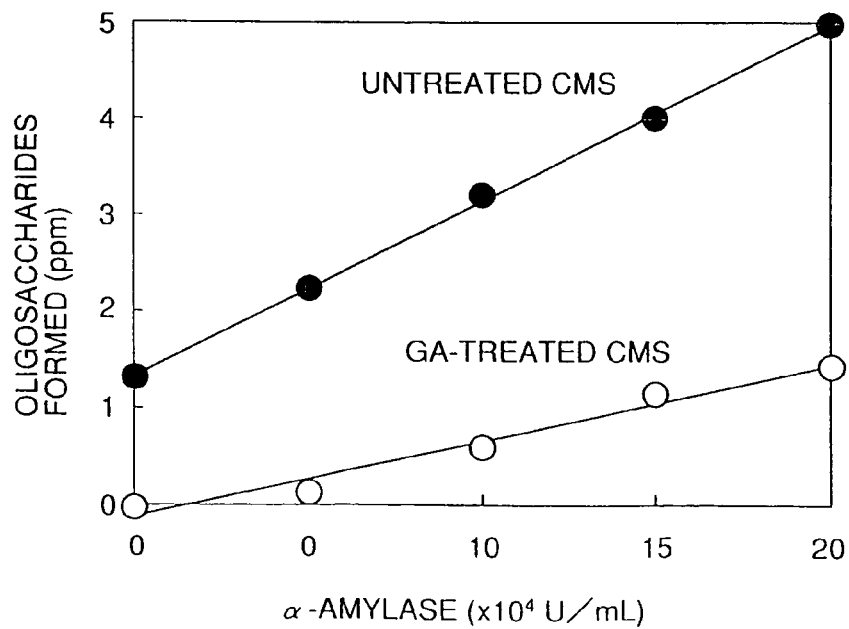
FIG. 7 is a diagram showing the results of Example 12, i.e., a graphic representation demonstrating the reactivity of α-amylase to a glucoamylase-treated CM-starch (obtained in Example 9) and a non-glucoamylase-treated CM-starch (a comparative example) in a solution (dispersion) system.

As shown in FIG. 7, the CM-starch treated in advance with glucoamylase had the reactivity to the α-amylase (an endo-reaction type enzyme)(the inclination of the calibration curve in the diagram), was about one half of that of the CM-starch not treated in advance. While the background value of the untreated CMS was about 1.3 ppm, that of the GA-treated CMS was nearly zero.

The fact that the content of oligosaccharide produced from the untreated CMS was not zero while the content of α-amylase was zero may be explained by the following supposition. The vertical axis of the data of FIG. 7 is the scale of oligosaccharide formed, however, in the reaction system of the present example, the amount of the ultimately produced glucose was analyzed. Although the residues of CMS (CM-starch) remaining after the reaction with the α-amylase were removed by centrifugation, minute amounts of CMS particles survived in the supernatants. When the minute amounts of CMS particles are suffered to mingle into the supernatants collected as the produced oligosaccharides, the CMS particles are also destined to be attacked by the glucoamylase contained in the coloration reaction solution B. In the untreated CMS, since the terminal glucose was not removed, the terminal glucose was hydrolyzed by the glucoamylase and consequently detected. Since the amount of the terminal glucose thus detected did not dependent on the amount of α-amylase used but was nearly constant, it was fated to raise the whole calibration curve as the background value in FIG. 7.

In contrast, the CM-starch treated in advance with the glucoamylase was devoid of an unmodified glucose terminal capable of reacting with glucoamylase which is an exo-active type enzyme. Even when the CMS particles are suffered to mingle into the coloration reaction system, they will not raise the background value.

The fact that the reactivity of the CM-starch with the α-amylase is lowered by the treatment with glucoamylase may be logically explained by the following supposition. The α-amylase exhibits reactivity to polysaccharides having not less than four molecules of glucose chain length. This reactivity increases in accordance as the degree of polymerization increases (the chain length gains in size). When the glucose unit in the sugar chain is carboxylmethylated at random, the part formed of continued glucose molecules to which the α-amylase exhibits high reactivity is inevitably decreased. As a result, the starch inherently has the reactivity thereof to the α-amylase lowered when it is carboxylmethylated. When the CM-starch is further treated with glucoamylase, the branched chains of the CM-starch are severally removed through decomposition from the non-reducing terminal. When CM sites are present halfway along the lengths of branched chains, they are hydrolyzed and removed by glucose units from the non-reducing terminal up to the sites. As a result, the CM-starch treated with the glucoamylase are converted into a kind of limit dextrins and the part formed of continued glucose molecules to which the α-amylase exhibits high reactivity is further decreased apparently. FIG. 7 demonstrates this fact.

Though the CM-starch treated in advance with glucoamylase has the reactivity with the α-amylase lowered as described above, it has the reactivity with the α-amylase increased in the dry assay element as demonstrated in Examples 13 and 14 to be cited herein below.

EXAMPLE 13

Reactivity of GA-Treated CMS with α-Amylase (Dry System)

A multi-layered analysis element identical in construction with that of Example 5 was prepared by faithfully repeating the procedure of Example 5 while using the glucoamylase-treated CM-starch obtained in Example 9 instead.

Specifically, slides identical in construction to those of Example 2 were prepared by faithfully repeating the procedure of Example 2 while using the glucoamylase-treated CM-starch obtained in Example 9 as the substrate layer in the place of the carboxylmethylated starch used in Example 2. Thereafter, in the same manner as in Example 5, on the tricot knitted cloth layer, which served both as a substrate layer and a spreading layer, an ethanol solution of the amylase-labelled CRP-IgG was coated and impregnated at a coverage of 3 mg/m$^2$, and then dried to prepare multi-layered immunoassay slide 5 for analysis of CRP (Example 13).

As a comparative example, a slide 6 example identical in construction to that of Example 13 was prepared by repeating the procedure of Example 13 while using an untreated carboxylmethylated starch as the substrate in the place of the glucoamylase-treated carboxylmethylated starch.

EXAMPLE 14

Figure 8:
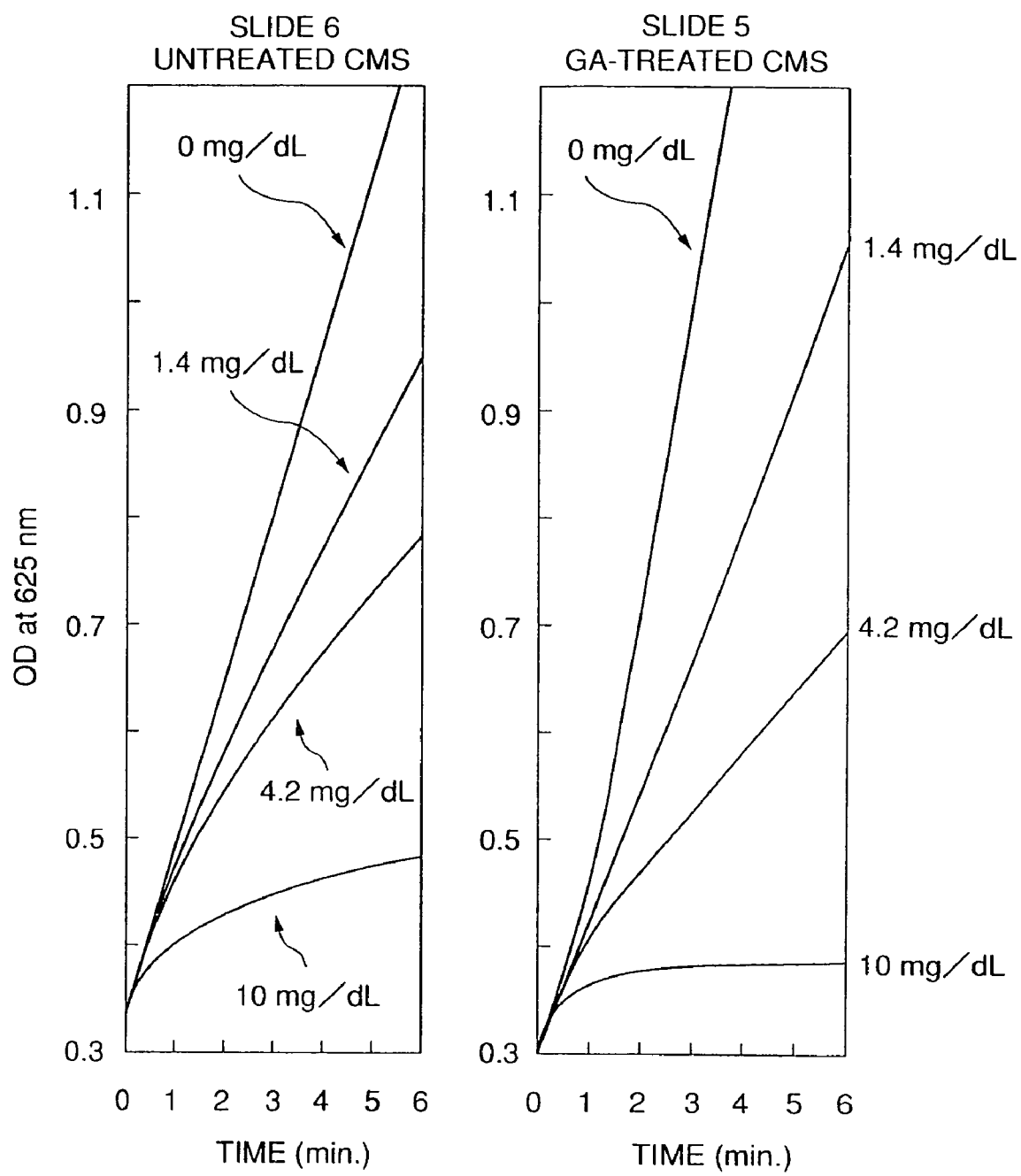
FIG. 8 is a diagram showing the results of Example 14, i.e., a graphic representation showing the time-course changes in reflected optical density obtained after a CRP solution of a varying concentration was spotted on a Slide 5 (prepared in Example 13) and a Slide 6 (a comparative example).

On the slide 5 and the slide 6, 10 µL for each of 50 mM glycerophosphorate buffer solution (pH 7) containing CRP in a varying concentration of 1, 1.4, 4.2, and 10 mg/dL was spotted. The slides were maintained at 37° C. and were measured from the support side along the course of time for reflected optical density at a wavelength of 625 nm. The time-course changes of reflected optical density after the spotting of the CRP solution are shown in FIG. 8.

When the CRP solution of 0 mg/dL is spotted, the hydrolytic activity with the CM-starch, a non-diffusible substrate, is maximized because the α-amylase in the labelled antibody is not subjected to the steric hindrance due to the binding with an antigen (CRP). The activity existent at the CRP concentration of 0 mg/dL at which the α-amylase exhibits the highest activity was notably high on the slide 5 (Example 14, the righthand side of FIG. 8) using the GA-treated CMS as compared with the comparative example (slide 6 using untreated CMS, on the lefthand side of FIG. 8). Based on the index of the slope of the time-course change of reflected optical density, the CM-starch treated in advance with glucoamylase showed about twice as high reactivity with the α-amylase as the untreated CM-starch.

When the steric hindrance to the α-amylase gained in intensity in accordance as the content of CRP, an antigen, the decline of the reactivity with the α-amylase was conspicuous on the slide 5 (Example 14, on the righthand side of FIG. 8) using the GA-treated CMS. This fact indicates that owing to the reactivity of the α-amylase with the CM-starch in the dry assay element, the change of the reflected optical density relative to the change of CRP concentration is increased and the sensitivity is enhanced by treating the starch in advance with glucoamylase and consequently rendering it specific to the endo-active type enzymatic reaction.

What is claimed is:

1. An immunoassay element for quantitatively analyzing an antigen by determining a change in enzymatic activity caused by any of followings:
   1) a reaction between the antigen and an enzyme-labelled antibody, the enzyme-labelled antibody being a conjugate of an antibody and a labelling enzyme, the antibody being capable to react and bind specifically with the antigen, wherein the antigen sterically hinders enzymatic activity in a specific binding complex of the antigen and the enzyme-labelled antibody;
   2) a reaction between the antigen, an antibody and an enzyme-labelled antigen, the enzyme-labelled antigen being a conjugate of an antigen and a labelling enzyme, wherein the antibody sterically hinders enzymatic activity in a specific binding complex of the antibody and the enzyme-labelled antigen; and
   3) a reaction between the antigen, an enzyme-labelled antibody and a conjugate of the antigen with a high molecular weight compound, the enzyme-labelled antibody being a conjugate of an antibody and a labelling enzyme, wherein the conjugate of the antigen with a high molecular weight compound sterically hinders enzymatic activity in a specific binding complex of the conjugate of the antigen with a high molecular weight compound and the enzyme-labelled antibody;

said element comprising:
   a substrate layer containing a non-diffusible substrate composed of polysaccharide which is capable of being fragmented by said labelling enzyme into a diffusible glucose oligomer which migrates from said substrate layer; and
   a reagent layer containing a fragmenting enzyme for further fragmenting said diffusible glucose oligomer, which has migrated from said substrate layer, into a detectable glucose monomer, said substrate layer being superposed on said reagent layer;
   wherein said labelling enzyme is α-amylase, and said fragmenting enzyme is glucoamylase or α-glucosidase; and
   wherein said non-diffusible substrate is carboxylmethylated starch restrictively decomposed in advance with an exo-active glucosidase from the non-reducing terminal glucose site through the carboxylmethyl-modified glucose unit site or the glucose chain branching site so that said non-diffusible substrate reacts solely with said labelling enzyme and avoids reacting with said fragmenting enzyme.

2. The immunoassay element according to claim 1, wherein said reagent layer is formed of a layer containing a hydrophilic polymer as the binder.

3. The immunoassay element according to claim 1, wherein said substrate layer is a porous layer formed of a porous medium.

4. The immunoassay element according to claim 1, wherein said enzyme labelled antibody is contained in said substrate layer or a layer superposed on said substrate layer.

5. The immunoassay element according to claim 1, wherein said antibody is contained in said substrate layer or a layer superposed on said substrate layer.

6. The immunoassay element according to claim 1, wherein said enzyme labelled antigen is contained in said substrate layer or a layer superposed on said substrate layer.

7. The immunoassay element according to claim 1, wherein said antibody and said enzyme labelled antigen are contained in said substrate layer or a layer superposed on said substrate layer.

8. The immunoassay element according to claim 1, wherein said conjugate of the antigen with the high molecular weight compound and said enzyme labelled antibody are contained in said substrate layer or a layer superposed on said substrate layer.

9. The immunoassay element according to claim 1, further comprising a reagent composition for reacting with said detectable glucose monomer to form a dye having an absorption peak in the visible wavelength range and contained in said reagent layer or another water permeable layer.

10. The immunoassay element according to claim 9, wherein the reagent composition contains a leuco dye which colors upon oxidation.

11. The immunoassay element according to claim 10, wherein said reagent layer contains a hydrophilic binder, and the reagent composition contains a dispersion of a solution of leuco dye in a water insoluble solvent in the hydrophilic binder.

12. The immunoassay element according to claim 11, wherein said reagent composition contains a peroxidase and the leuco dye.

13. An immunoassay element for quantitatively analyzing an antibody by determining a change in enzymatic activity caused by any of followings:
- a reaction between the antibody and an enzyme-labelled antigen, the enzyme-labelled antigen being a conjugate of an antigen and a labelling enzyme, the antibody being capable to react and bind specifically with the antigen, wherein the antibody sterically hinders enzymatic activity in a specific binding complex of the antibody and the enzyme-labelled antigen; and
- a competitive reaction between the antibody, an antigen and an enzyme-labelled antibody, the enzyme-labelled antibody being a conjugate of an antibody and a labelling enzyme, wherein the antigen sterically hinders enzymatic activity in a specific binding complex of the antigen and the enzyme-labelled antibody;

said element comprising:
- a substrate layer containing a non-diffusible substrate composed of polysaccharide which is capable of being fragmented by said labelling enzyme into a diffusible glucose oligomer which migrates from said substrate layer; and
- a reagent layer containing a fragmenting enzyme for further fragmenting said diffusible glucose oligomer, which has migrated from said substrate layer, into a detectable glucose monomer, said substrate layer being superposed on said reagent layer;
- wherein said labelling enzyme is α-amylase, and said fragmenting enzyme is glucoamylase or α-glucosidase; and
- wherein said non-diffusible substrate is carboxylmethylated starch restrictively decomposed in advance with an exo-active glucosidase from the non-reducing terminal glucose site through the carboxylmethyl-modified glucose unit site or the glucose chain branching site so that said non-diffusible substrate reacts solely with said labelling enzyme and avoids reacting with said fragmenting enzyme.

14. The immunoassay element according to claim 13, wherein said reagent layer is formed of a layer containing a hydrophilic polymer as the binder.

15. The immunoassay element according to claim 13, wherein said substrate layer is a porous layer formed of a porous medium.

16. The immunoassay element according to claim 13, wherein said enzyme labelled antibody is contained in said substrate layer or a layer superposed on said substrate layer.

17. The immunoassay element according to claim 13, wherein said antibody is contained in said substrate layer or a layer superposed on said substrate layer.

18. The immunoassay element according to claim 13, wherein said enzyme-labelled antigen is contained in said substrate layer or a layer superposed on said substrate layer.

19. The immunoassay element according to claim 13, wherein said antibody and said enzyme labelled antigen are contained in said substrate layer or a layer superposed on said substrate layer.

20. The immunoassay element according to claim 13, further comprising a reagent composition for reacting with said detectable glucose monomer to form a dye having an absorption peak in the visible wavelength range and contained in said reagent layer or another water permeable layer.

21. The immunoassay element according to claim 20, wherein the reagent composition contains a leuco dye which colors upon oxidation.

22. The immunoassay element according to claim 21, wherein said reagent layer contains a hydrophilic binder, and the reagent composition contains a dispersion of a solution of leuco dye in a water insoluble solvent in the hydrophilic binder.

23. The immunoassay element according to claim 22, wherein said reagent composition contains a peroxidase and the leuco dye.

* * * * *